United States Patent [19]

McCook et al.

[11] Patent Number: 5,690,948

[45] Date of Patent: Nov. 25, 1997

[54] ANTISEBUM AND ANTIOXIDANT COMPOSITIONS CONTAINING GUGULIPED AND ALCOHOLIC FRACTION THEREOF

[75] Inventors: John Patrick McCook, Guilford; Joseph Michael Corey, Waterbury; Peter Ladislaus Dorogi, Norwalk, all of Conn.; John Steven Bajor, Ramsey, N.J.; Helen Elizabeth Knaggs, Weehawken, N.J.; Beth Anne Lange, Woodbridge, N.J.; Erwin Sharpe, West New York, N.J.

[73] Assignee: Elizabeth Arden Co., Division of Conopco, Inc., New York, N.Y.

[21] Appl. No.: 781,767

[22] Filed: Jan. 10, 1997

[51] Int. Cl.⁶ .......................... A61K 7/48; A61K 35/78; A61K 47/28; A61K 47/46
[52] U.S. Cl. .................. 424/401; 424/195.1; 424/78.03; 424/59; 514/943
[58] Field of Search .................. 424/401, 195.1, 424/78.03, 59; 514/943

[56] References Cited

U.S. PATENT DOCUMENTS

| | | | |
|---|---|---|---|
| 4,847,069 | 7/1989 | Bissett et al. | 424/47 |
| 4,847,071 | 7/1989 | Bissett et al. | 424/59 |
| 5,273,747 | 12/1993 | Bombardelli et al. | 424/195 |
| 5,521,223 | 5/1996 | Piazza et al. | 514/785 |
| 5,587,176 | 12/1996 | Warren et al. | 424/443 |
| 5,620,965 | 4/1997 | Blank | 514/159 |

FOREIGN PATENT DOCUMENTS 447 706  9/1991  European Pat. Off. .

OTHER PUBLICATIONS

Cunliffe et al., "Tropical Benzoyl Peroxide Increases The Sebum Excretion Rate In Patients With Acne", British Journal of Dermatology (1983) 109, 577–579.
W.J. Cunliffe, "Acne", p. 256, Martin Dunitz Ltd., 1989.
"Guggal", Herbs and Medicinal Plants, pp. 183–184.
Sheela et al. 1995 Indian Journal of Experimental Biology 33 (5) pp. 337–341, May 1, 1995.
Singh et al. 1994 Cardiovascular Drugs and Therapy 8 (4) pp. 659–664, Apr. 1, 1994.
Joseph et al. 1994 Insect Science and its application 15 (2) pp. 197–202, Apr. 1, 1994.

*Primary Examiner*—Marian C. Knode
*Assistant Examiner*—Mary K. Zeman
*Attorney, Agent, or Firm*—Rimma Mitelman

[57] ABSTRACT

Gugulipid (a lipophilic ethyl acetate extract from C. mukul or C. wightii) and an alcoholic fraction of gugulipid as antisebum and/or antioxidant active in cosmetic skin care compositions and methods is disclosed. Gugulipid from C. mukul and its alcoholic fraction are capable of delivering dual benefit to the skin: controlling or preventing sebum secretion (oily skin conditions) and protecting the skin from free radical damage.

7 Claims, No Drawings

ANTISEBUM AND ANTIOXIDANT COMPOSITIONS CONTAINING GUGULIPED AND ALCOHOLIC FRACTION THEREOF

FIELD OF THE INVENTION

Methods and compositions for controlling or preventing sebum secretion from sebocytes, for controlling or preventing oily skin conditions, and also for protecting skin from free radical activity.

BACKGROUND OF THE INVENTION

Sebum is skin oil which is produced by sebocytes (cells of the sebaceous glands in the skin) and is then secreted to the skin surface. Excessive amount of sebum on the skin surface results in the condition known as "oily skin." Oily skin is associated with a shiny, undesirable appearance and a disagreeable tactile sensation. Many methods and compositions exist which attempt to control the excessive sebum secretion, but none have proved totally satisfactory.

Formation of free radicals in the skin does not appear to be related to the sebum secretion. Low levels of free radicals are formed in the skin as part of the natural metabolic pathways. The level of free radicals is increased in response to UV radiation and other environmental oxidants, e.g. pollution and cigarette smoke. Increased concentration of free radicals leads to lipid peroxidation in skin cells and cellular damage, which in turn results in a premature ageing of the skin with an accompanying loss of firmness and elasticity, wrinkles, discoloration, age spots, and dryness. Antioxidants, such as vitamin E (alpha-tocopherol), decrease the level of free radicals in the skin.

Cosmetic actives which provide more than one benefit are highly desirable, both from the manufacturer's and consumer's perspective.

Guggal is obtained from a gum/resin of the plant Commiphora mukul (shrubs or trees) or Commiphora wightii. Guggal contains a complex mixture of terpenes, sterols, esters and higher alcohols. The ethyl acetate extract of the resin is an oily resinous material known as "gugulipid" or "guggal lipid." Gugulipid has been used medicinally in the treatment of obesity and elevated cholesterol levels. The medicinal activity of gugulipid is attributed to two known ketonic steroids (guggulsterones).

Bombardelli et al. (U.S. Pat. No. 5,273,747) discloses the anti-inflammatory activity of gugulipid and a guggulsterone-enriched fraction thereof and their use in the treatment of benign prostatic hypertrophy and in the treatment of acne. In this regard it is important to note that although increased sebum production may be one of the many factors that lead to the formation of acne, an anti-acne agent does not necessarily possess antisebum activity. For instance, benzoyl peroxide and salicylic acid are well-established anti-acne agents, but they do not decrease sebum output. See Cunliffe, et al., "Topical Benzoyl Peroxide Increases The Sebum Excretion Rate In Patients With Acne", British Journal of Dermatology (1983) 109, 577–579; William J. Cunliffe, "Acne", p. 256, Martin Dunitz Ltd. (1989). See also Comparative Example 3 hereinbelow. Furthermore, the guggulsterone-enriched fraction described by Bombardelli was obtained with ethyl acetate, as contrasted to the alcoholic fraction employed in the present invention.

Bissett et al. (U.S. Pat. Nos. 4,847,071 and 4,847,069) and Piazza et al. (U.S. Pat. No. 5,521,223) disclose photoprotective and anti-wrinkle compositions containing guggal as a natural anti-inflammatory. Although some compounds may be anti-inflammatory through antioxidant pathways, not all anti-inflammatory mechanisms are antioxidant mediated, nor are all antioxidant antiinflammatory. Put another way, antiinflammatory and antioxidant effects do not necessarily follow each other.

The art discussed above does not address the need for an agent which contains both antisebum and antioxidant activities. The art does not disclose either antisebum or antioxidant activity of guggal or gugulipid or fractions thereof. Furthermore, as far as fractions of gugulipid are concerned, the art discloses the preparation and use of only a guggulsterone-enriched (ethyl acetate) fraction. The preparation, use and activities of an alcoholic fraction are not disclosed.

SUMMARY OF THE INVENTION

The present invention includes in its first aspect a method of controlling or preventing an oily skin conditions, especially in the facial area, by applying to the skin a composition comprising gugulipid and/or alcoholic fraction thereof in a cosmetically acceptable vehicle.

The second aspect of the present invention includes a method of reducing, preventing or controlling sebum secretion from sebocytes by applying to the skin a composition comprising gugulipid and/or alcoholic fraction thereof in a cosmetically acceptable vehicle.

Another aspect of the invention is a method of protecting the skin from free radical activity (i.e., relieving the oxidative stress in the skin) by applying to the skin a composition comprising gugulipid and/or alcoholic fraction thereof in a cosmetically acceptable vehicle.

Still another aspect of the invention is a method of simultaneously controlling or preventing sebum secretion while also protecting the skin from free radical damage, by the use of a single active agent: gugulipid or an alcoholic fraction thereof.

Yet another aspect of the invention is a method for the manufacture of an alcoholic fraction of gugulipid.

Still another aspect of the invention is a cosmetic composition for care of the skin, the composition comprising an alcoholic fraction of gugulipid in a cosmetically acceptable vehicle.

The inventive methods and compositions provide control of sebum secretion from sebocytes, improved oil control and improved skin feel, prevent shine and stickiness, while also protecting the skin from damaging free radical activity, which results in reduced appearance of wrinkles and aged skin, improved skin color, treatment of photoaged skin, improvement in skin's radiance and clarity and finish, and an overall healthy and youthful appearance of the skin.

DETAILED DESCRIPTION OF THE INVENTION

Except in the operating and comparative examples, or where otherwise explicitly indicated, all numbers in this description indicating amounts of material or conditions of reaction and/or use are to be understood as modified by the word "about." All amounts are by weight of the final composition, unless otherwise specified.

The term "skin" as used herein includes the skin on the face, neck, chest, back, and scalp.

Gugulipid and non-guggulsterone fraction thereof:

The term "gugulipid" as used herein means an ethyl acetate extract of gum/resin guggal from the tree C. mukul or C. wightii.

The term "alcoholic fraction" as used herein means a highly polar, non-aqueous fraction of gugulipid. Preferably, the alcoholic fraction is of non-pet ether fraction of gugulipid.

The inventive methods of controlling sebum secretion, controlling oily skin and/or protecting skin from free radicals employs gugulipid and/or an alcoholic fraction thereof. It has been found, as part of the present invention that gugulipid and an alcoholic fraction thereof possess a rare quality of providing a dual benefit for skin care, i.e. both antisebum and antioxidant activity. It has been found that an aqueous extract of guggal from C. mukul have little or none of antisebum and/or antioxidant activity observed with the ethyl acetate extract of guggal from C. mukul. It has also been found that the antisebum and/or antioxidant activity of gugulipid is concentrated in an alcoholic fraction of gugulipid, rather than an ethyl acetate guggul-sterone enriched fraction described by Bombardelli.

Gugulipid may be obtained from the following suppliers:
C. Mukul extract:
Indena (80 E Route 4, Paramus, N.J., 07652) Pt. Cosmetique Java, Bogar (Campo R&D, Singapore)(C. wightii extract also available).

According to the present invention, from 0.001 to 10 wt. % of gugulipid is employed, by weight of the composition, preferably from 0.001 to 3 wt. %, and most preferably from 0.01 to 2 wt. %.

When an alcoholic fraction is employed, it may advantageously be employed in a lower amount than gugulipid to provide the same activity as may be obtained with higher amounts of gugulipid itself. The inventive methods and compositions may employ from 0.0001 to 5 wt. %, preferably from 0.001 to 3 wt. %, and most preferably from 0.01% to 2 wt. % of an alcoholic fraction of gugulipid.

The alcoholic fraction may be obtained by subjecting gugulipid or, preferably, the non-pet ether fraction of gugulipid to separation (e.g., by extraction or eluting with a highly polar, non-aqueous solvent. Typical suitable solvents are alcohols, preferably low chain (i.e., less than 6 carbons) alcohols, i.e. methanol, ethanol, propanol, isopropanol, butanol, 2-butanol, 1-pentanol, 2-pentanol, 3-pentanol, 1-hexanol. The obtained fraction is preferably dried, e.g. by evaporation or freeze-drying to concentrate the active amount.

The alcoholic fraction employed in the inventive methods of compositions generally contains less than 99% alcohol, by weight of the fraction, preferably less than 25%, most preferably less than 5%.

The alcoholic fraction contains little or no of cis guggulsterone (also known as guggulsterone E) described by Bombardelli. It has been unexpectedly found, as part of the present invention, that cis-guggulsterone does not provide either antioxidant or antisebum activity. Consequently, the antisebum and/or antioxidant activity of gugulipid is due to active compounds other than cis-guggulsterone and is found concentrated in an alcoholic fraction of gugulipid. The alcoholic fraction according to the present invention contains less than 0.1% of cis-guggulsterone by weight of the fraction, and preferably less than 0.05% % of cis-guggulsterone. The guggulsterone amount in a fraction may be checked by HPLC, mass spectroscopy or TLC.

Cosmetically Acceptable Vehicle:

The compositions according to the invention also comprise a cosmetically acceptable vehicle to act as a diluant, dispersant or carrier for gugulipid and/or the alcoholic fraction thereof in the composition, so as to facilitate its distribution when the composition is applied to the skin.

The vehicle may be aqueous, anhydrous or an emulsion. Preferably, the compositions are aqueous or an emulsion, especially water-in-oil or oil-in-water emulsion. Water when present will be in amounts which may range from 5 to 99%, preferably from 20 to 70%, optimally between 35 and 60% by weight.

Besides water, relatively volatile solvents may also serve as carriers within compositions of the present invention. Most preferred are monohydric $C_1$-$C_3$ alkanols. These include ethyl alcohol, methyl alcohol and isopropyl alcohol. The amount of monohydric alkanol may range from 1 to 70%, preferably from 10 to 50%, optimally between 15 to 40% by weight. The alcohol content of the alcoholic fraction of the gugulipid is not included in these amounts.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols. (3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

Optional Skin Benefit Materials and Cosmetic Adjuncts:

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants. Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Various types of active ingredients may be present in cosmetic compositions of the present invention. Actives are defined as skin benefit agents other than emollients and other than ingredients that merely improve the physical characteristics of the composition. Although not limited to this category, general examples include anti-acne agents, additional anti-sebum agents, and sunscreens.

Anti-acne agents include but are not limited to benzoyl peroxide (up to 20 wt. % may be included), retinoids (typically 0.025%–0.05%), salicylates acid (typically up to 2 wt. %), and sulphur (up to 8 wt. %).

Other antisebum actives may be included, most preferably tridecyl salicylate (or zinc pyriphione) in an amount up to 10 wt. %.

Retinol or esters thereof may be included to provide various skin benefits. Suitable retinol esters include retinol palmitate, retinol acetate, and retinol linoleate. Retinol linoleate is especially preferred to provide additional anti-sebum activity and anti-aging benefits. The amounts of retinol and/or retinol esters are in the range of from 0.001 wt. % to 3 wt. % by weight of the composition, preferably from 0.001 wt. % to 0.5 wt. %.

An especially preferred combination of an active (gugulipid or an alcoholic fraction thereof) is with an optional ingredient selected from the group consisting of tridecyl salicylate, retinyl linoleate and mixtures thereof, in order to provide maximum antisebum activity, anti-aging and optimum healthy-looking skin.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the composition.

Powders may be incorporated into the cosmetic composition of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor ingredients may range anywhere from 0.001% up to 20% by weight of the composition.

Use of the Composition:

The composition according to the invention is intended primarily as a product for topical application to human skin, especially as an agent for controlling or preventing oily skin, for improving skin's radiance and clarity and finish, and for preventing or reducing the appearance of wrinkled, dry, aged or photoaged skin.

In use, a quantity of the composition, for example from 1 to 100 ml, is applied to exposed areas of the skin, from a suitable container or applicator and, if necessary, it is then spread over and/or rubbed into the skin using the hand or fingers or a suitable device.

Product Form and Packaging:

The topical skin composition of the invention can be in any form, e.g. formulated as a lotion, a fluid cream, or a cream. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,507, incorporated by reference herein.

The following specific examples further illustrate the invention, but the invention is not limited thereto.

EXAMPLE 1

This example demonstrates the procedure for the fractionation of gugulipid into fractions of increasing polarity.
Materials:
Gugulipid (Lot No. 42941, Lipo Chemicals Inc. Paterson N.J.)
Medium pressure column (5 cm i.d×62 cm in length).
Silica (gel, Merck), Aldrich, Cat no. 22,719-6, Grade 9385, 230,400, mesh 60 A.
TLC plates, LHP-kk 20×10 cc Lot#004966, Cat#4805-711 Whatman.
Hexane, HPLC grade (Fisher)
Ethyl Acetate, HPLC grade (Fisher)
Methanol, HPLC grade (Fisher)
Chloroform, HPLC grade (Fisher)
Phosphoric Acid (Fisher)
Cupric Sulfate $CuSO_4$ (Fisher)
Petroleum Ether (Fisher)
24 Beakers (400 ml)
Scintillation Vials
Capillary tubes (5 µl)
2 Graduated cylinders (2000 ml)
1 Developing dish
1 Oven (Napco Model 420)
1 Hot/stir plate
2 Round bottom Flasks (500 ml)
Rotary Evaporator
Water (Milli-Q Water)
Method:

1. Weighed 5.0672 g of Gugulipid into a 500 ml round bottom flask.
   (A) Dissolved Gugulipid in 100 ml of Ethyl Acetate (to make a slurry).
   (B) The Ethyl Acetate was pulled off using the Rotary Evaporator.
   (C) Added 350 ml of Pet Ether to the flask.
   (D) Mixture was allowed to stir overnight.
2. Filled medium pressure column up to 75% with Silica (Merck), and prepared the column by washing with 700 ml of Hexane/Ethyl Acetate (10:1 ratio).
3. Removed flask from stir plate and decanted the Pet Ether into a 500 ml round bottom flask.
   (A) The Pet Ether was pulled off using the rotavapor until approx. 3 ml remained.
   (B) The remaining 3 ml was quantitatively transferred to a scintillation vial for which a tare weight had been previously recorded.
   (C) Sample was evaporated to dryness under the hood.
   (D) Final tare weight was recorded, and sample labeled (Pet Ether non-polar fraction#1)
4. Dissolved the remaining residue from the Pet Ether extraction in 50 ml of Ethyl Acetate, and transferred it to the medium pressure column using a glass Pasteur pipet.
5. Fraction 2 was eluted from the column with 800 ml of Hexane/Ethyl Acetate, 7:1 ratio.
6. Fractions 3–5 were eluted with Hexane/Ethyl Acetate at a 5:1 ratio. Each fraction was approximately 200 ml.
7. Fractions 6–12 were eluted with 1500 ml Hexane/Ethyl Acetate at a 2:1 ratio.
8. Fractions 13–19 were eluted from the column with 2000 ml Hexane/Ethyl Acetate, 1:1 ratio.
9. Fractions 20–29 were eluted with 3000 ml Hexane/Ethyl Acetate, 1:2 ratio.
10. Fractions 30–37 were eluted with 2000 ml Hexane/Ethyl Acetate, 1:3 ratio.
11. Fractions 38–41 were eluted with 100% Ethyl Acetate.
12. Fraction 42 was eluted with 100% methanol (1000 ml).
13. Fractions 43 and 44 were eluted with 100% methanol (1000 ml).
14. All fractions were evaporated down to approximately 10 ml using a steam bath and transferred into scintillation vials.
15. Fractions 1–44 were analyzed by Thin Layer Chromatography (TLC).
    (A) TLC plates were developed using Chloroform/Methanol 9:1 ratio.
    (B) TLC plates were stained with 10% Copper Sulfate in 8% Phosphoric Acid.
16. Due to poor TLC results fractions 26–39 were concentrated and reanalyzed.
17. Fractions which were similar in TLC profile were pooled. The following fractions were pooled.

Fractions 9, 10, and 11
    Fractions 13, and 14
    Fractions 16, 17, and 18
    Fractions 19, and 20
    Fractions 22, 23, and 24
    Fractions 40, 41, and 42 (but these contained 99% of fraction 42, due to the extremely small sample size of fractions 40 and 41)

18. Fractions 26–39, and the pooled fractions were reanalyzed by TLC.
19. Fractions that were similar in TLC profile and which were combined:

Fractions 26, and 27
    Fractions 30, 31, and 32
    Fractions 34, and 35

20. The remaining fractions were evaporated to dryness under the hood and delivered to the submitter. A total of eighteen sample fractions resulted.
21. Fractions which did not show any spots by TLC were discarded.

Results:

Starting with 5.06 g of gugulipid (350 ml pet ether), fraction 1 (1.7469 g) was obtained as the pet ether soluble fraction. The fraction not soluble in pet ether was dissolved in 50 ml of Ethyl Acetate and transferred onto the silica column (5 cm i.d×62 cm in length) and eluted with solvent portions of increasing polarity. This resulted in 43 further fractions. Based on similar TLC profiles, several fractions were combined. Fractions 26–29 contained very little material and had to be concentrated before TLC results could be obtained. From the multiple bands on the TLC plates it was clear that most fractions contain several compounds. Some fractions were more concentrated than others as apparent from the intense bands on the TLC plates. 18 fractions resulted.

Fractions 43 and 44 were the only fractions that contained solely methanolic extract. Fraction 42 was eluted with methanol, but was combined with fractions 40 and 41 (which were eluted with ethyl acetate, but were very small in size). Fraction 42 actually contained about 99% of fraction 42 and about 1% of fractions 40 and 41. Fraction 44 contained substantially less active ingredient than fractions 42 and 43, because it was an end portion of the alcoholic fraction.

EXAMPLE 2

This example reports an in vitro analysis of sebum suppression of gugulipid and various fractions thereof.

In Vitro Sebocyte Lipogenesis Assay

Human sebaceous glands were isolated from the nose of a male (age 60) and cultured using submerged tissue culture techniques (Bajor et al, *J. Invest. Dermatol.* 102: 1994, P. 564). These sebocytes accumulate intracellular lipid droplets characteristic of mature human sebum.

Harvested and passaged sebocytes were added to each well of a 48 well tissue culture plate and incubated at 37° C. in the presence of 7.5% $CO_2$ for 10 days, On the day of experimentation, the growth medium was removed and the sebocytes washed three times with phosphate buffered saline (PBS). Fresh PBS in 0.5 ml amount was added to each well and 10 µl of a test agent, at various concentrations as indicated in Table 1. Triplicate wells were utilized for each sample. Controls consisted of PBS, dimethyl sulfoxide (DMSO) used to solubilize the lipophilic compounds, and phenol red, a compound which possesses estrogen-like activity (Phenol Red decreases sebum secretion and was used as a control to verify the integrity of the sebocyte assay). The cultures were incubated at 37° C./7.5% $CO_2$ for 30 minutes. Radioactive label was prepared by adding 100 µl of $^{14}C$ labelled acetic acid (Amersham, sodium salt, specific activity of 56 mCi/mmol) to 10 ml of 50 mM sodium acetate buffer. Then, 50 µl was added to each well containing the sebocytes and test agents. The cultures were returned to the incubator for four hours. Thereafter, the sebocytes were rinsed three times with fresh PBS to remove unbound active and radioactive label. Radioactive label remaining in the cultured sebocytes was counted using a Beckman scintillation counter. The results were expressed as % reduction compared to control (DMSO).

To determine whether a fraction contained cis-guggulsterone, a sample of each fraction was applied to the lower left corner of a separate 10×10 cm high performance silica gel plate. Samples were first developed to 9 cm in a running phase of hexane:ethyl acetate (50:50), air died, turned 90 degrees, then developed to 9 cm in chloroform:methanol (95:5). Plates were dried, immersed into a solution of 10 % copper sulfate/8% phosphoric acid, and heated to 185° C. for 10 minutes. A standard of cis-Guggulsterone (Steraloids, Inc.) was used as a reference.

The results that were obtained are summarized in Table 1.

TABLE 1

| Fraction # | Guggulsterone presence | 0.05% % Red'n (SD) | 0.01% % Red'n (SD) | 0.05% % Red'n (SD) | 0.10% % Red'n (SD) |
|---|---|---|---|---|---|
| Complete Gugulipid | ++ | 37.8* (8.1) | 52.8* (7.2) | 62.6* (6.0) | 66.3* (4.0) |
| 0 (Pet Ether) | ++ | −1.8 (13.6) | 47.1* (16.3) | 63.6* (1.4) | 78.2 (0.9) |
| 10 | ++ | — | — | −3.8(3.5) | 19.2* (4.5) |
| 14 | ++ | — | — | 18.1 (4.3) | 13.1 (8.1) |
| 15 | +++ | — | — | 17.8 (5.6) | 20.0* (4.3) |
| 16 | ++++ | — | — | 39.9* (0.1) | 38.6* (2.3) |
| 20 | + | — | — | 27.5* (3.3) | 32.1 (3.0) |
| 21 | ?[1] | 23.9* (3.9) | 26.3* (4.3) | 62.6* (5.8) | 64.3* (6.6) |
| 22 | ? | 31* (4.9) | 46.1* (4.9) | 65.9* (3.8) | — |
| 24 | ? | 35.5* (3.8) | 43.9* (9.1) | 50.6* (5.2) | 67.5* (1.1) |
| 27 | — | 38.7* (6.6) | 36.0* (11.1) | 63.5* (4.6) | 74.0* (2.3) |
| 28 | — | 38.4* (11.4) | 59.6* (6.0) | — | 69.0* (2.5) |
| 32 | — | 39.3* (4.4) | 50.2* (4.9) | 65.4* (0.4) | 78.3* (0.6) |
| 33 | — | 29.1* (9.7) | 34.3* (8.2) | 65.9* (3.8) | 68.5* (2.9) |
| 35 | — | 27.8 (13.7) | 32.3* (13.4) | 70.9* (2.3) | — |
| 40–42 (99% of 42) | — | 56* (5.2) | 60.1* (12.2) | 64.3* (6.6) | 71.8* (8.6) |
| 43 | ? | 49.4* (5.5) | 68.5* (5.5) | 64.9* (6.1) | 78.3* (0.6) |

TABLE 1-continued

| Fraction # | Guggulsterone presence | 0.05% % Red'n (SD) | 0.01% % Red'n (SD) | 0.05% % Red'n (SD) | 0.10% % Red'n (SD) |
|---|---|---|---|---|---|
| 44 | — | 25* (7.7) | 44.6* (9.2) | 75.1* (1.6) | 73.1* (0.9) |
| Phenol Red | — | — | — | — | 40.9* (2.5) |

*statistically significant results compared to control (DMSO) at $p < 0.01$ (calculated using student T-test)
¹"?" indicates migration to a similar area in the chromatogram but unclear if it is the cis-guggulsterone (it charred a different color). The level present was extremely low.

The analysis of the results in Table 1 is most meaningful at the lowest concentration tested, because at higher concentrations in vitro sebocyte viability may be compromised, and also at higher concentrations, even a poor antisebum active which may be present in a non-alcoholic fraction may deliver a relatively high activity. It is evident from the results in Table 1 that at the lowest concentration tested (0.005%) fractions 42 and 43 (alcoholic fractions) were the most active in suppressing sebum production. These fractions do not appear to contain any cis-guggulsterone. The reduced activity of fraction 44 compared to fractions 42 and 43 is probably due the reduced concentration of any guactive material, because fraction 44 was the end portion of the alcoholic fraction.

The in-vitro sebocyte assay was repeated for oil soluble extract of C. wightii. The results that were obtained are in Table 1A.

TABLE 1A

| Treatment | Concentration | % Reduction | STD DEV |
|---|---|---|---|
| C. wightii extract (Oil Soluble) | 0.01% | 40.6 | 9.4 |
|  | 0.10% | 44.9 | 4.4 |

It can be seen from Table 1A that oil soluble C. wightii extract also decreased sebum secretion.

COMPARATIVE EXAMPLE 3

The sebocyte assay described in Example 2 was repeated with various compounds as indicated in Table 2. All compounds in Table 2 are outside the scope of the invention.

The results that were obtained are summarized in Table 2. Negative values indicate increase in sebum production.

TABLE 2

| Treatment | Concentration | % Reduction | STD DEV |
|---|---|---|---|
| Estradiol | 0.0028% (100 μM) | 39.7 | 7.9 |
| Dihydrotestosterone | 0.00003% (1 μM) | −28.8 | 4.1 |
| Salicyclic Acid | 0.14% (10.0 mM) | 3.6 | 7.4 |
|  | 0.10% | −46.6 | 12.4 |
| cis-guggalsterone | 0.05% | 2.7 | 8.1 |
|  | 0.01% | 2.7 | 8.8 |

The results in Table 2 demonstrate that the sebocyte assay is a valid and reliable test for measuring sebum suppression, because estradiol (estrogen-like compound) provided sebum suppression, as predicted from the other sources, whereas dihydrotestosterone (androgen) actually increased sebum production, as also predicted from other sources. Salicylic acid, a known anti-acne agent did not inhibit sebum output, demonstrating that an antiache agent does not necessarily have antisebum activity. Cis-guggulsterone did not reduce sebum secretion, indicating that an active in gugulipid and in the alcoholic fraction thereof which provides antisebum activity is not cis-guggulsterone.

EXAMPLE 4

This example reports a chemical assay and an in vitro analysis of antioxidant activity of gugulipid and various fractions thereof.

Chemical Assay:

Chemical assay measures the antioxidant activity of various test compounds indicated in Table 3 (each tested at a concentration of 0.08%). 2,2'azino-di-[3-ethylbenzthialoine sulphonate] (6.1 μmol/l) and metmyoglobin (610 μmol/l) were solubolized in phosphate buffered saline (5mmol/l, pH 7.4). Test materials were then added and absorbance was measured at 734 nm before and after addition of the substrate, hydrogen peroxide (250 μmol/l). The initial absorbance was subtracted from the substrate containing absorbance. This prevents discrepancies in absorbance due to the test compound itself. The absorbance changes with time, thus multiple time points were examined. Results were expressed as % oxidation relative to a control containing all assay components but deionized water instead of test reagent (100% oxidation). A high number means no prevention of oxidation, a poor antioxidant. The antioxidant activity of Trolox (registered trademark of Hoffman-LaRoche), a water soluble form of vitamin E was measured to establish the validilty of the test. Trolox was purchased from Aldrich (2.5 mmol/l). C. wightii (lipophilic extract) was obtained from Campo.

The results that were obtained are summarized in Table 3.

TABLE 3

| TEST MATERIAL | % oxidation (±STD) at 3 minutes relative to water control | % oxidation (±STD) at 6 minutes relative to water control | % oxidation (±STD) at 9 minutes relative to water control |
|---|---|---|---|
| Trolox (water soluble vitamin E) | −0.70 (±0.5)* | 15.8 (±2.1)* | 44.6 (±2.1) |
| Total Guggulipid | 2.8 (±1.1)* | 4.4 (±0.08)* | 5.1 (±0.6)* |
| Fraction #0 | 60.7 (±8.3) | 72.5 (±4.7) | 73.8 (±0.9) |
| Fraction #10 | 82.9 (±3.5) | 88.7 (±2.3) | 88.2 (±0.2) |
| Fraction #14 | 98.4 (±1.0) | 99.4 (±0.9) | 111.1 (±16.7) |
| Fraction #15 | 94.6 (±0.6) | 96.5 (±0.3) | 94.4 (±2.0) |
| Fraction #16 | 97.6 (±4.7) | 93.8 (±5.2) | 87.9 (±8.4) |
| Fraction #20 | 65.8 (±14.7) | 71.2 (±8.3) | 70.1 (±1.7)* |
| Fraction #21 | 47.7 (±0.54)* | 49.9 (±0.6)* | 50.5 (±2.6) |
| Fraction #24 | 46.2 (±6.9) | 56.9 (±6.2) | 60.9 (±3.6)* |
| Fraction #27 | 79.8 (±7.1) | 78.0 (±4.6) | 77.2 (±2.1)* |
| Fraction #40–42 (99% of 42) | 18.7 (±3.1)* | 10.6 (±1.7)* | 9.2 (±0.7)* |
| Fraction #43 | −33.2 (±21.2)* | −4.5 (±2.2)* | −3.2 (±1.6)* |
| Fraction #44 | −12.6 (±8.6)* | −6.5 (±4.9)* | −4.4 (±3.4)* |
| cis-guggulsterone | 100 (±10.0 | 97.9 (±4.1) | 97.4 (±6.1) |
| C. Wightii | 85.6 (±0.0) | 98.0 (±5.3) | 99.9 (±7.1) | p-value was determined using Lotus 1-2-3 students t-test.
*p-value < 0.05 (statistically significant compared to water control)

The results in Table 3 demonstrate that total gugulipid and fractions 42–44 had the best anti-oxidant activity, with fraction 43 having the highest activity. Cis-guggulsterone had a very inferior anti-oxidant activity, proving that it is other actives, not cis-guggulsterone, that impart anti-oxidant activity to gugulipid or to the alcoholic fraction of gugulipid. Neither C. wightii nor the aqueous extract of C. mukul had significant antioxidant activity. The chemical assay outlined above measures antioxidant activity obtained via direct free radical quenching, not via antiinflammatory pathway. The assay establishes that gugulipid and the alcoholic fraction thereof act as antioxidants via direct free radical quenching.

In general, the antioxidant capability measured chemically correlates with in vitro keratinocyte results (see Table 4 below).

In vitro antioxidant assay:

Lipid peroxidation is a well established mechanism of cellular injury, which occurs in both plants and animals. Cleavage of unsaturated fatty acids, including membrane lipids, leads to the production of byproducts such as aldehydes. The aldehydic byproducts malondialdehyde (MDA) and 4-hydroxyalkenals serve as convenient markers of lipid peroxidation.

Cell culture:

Human keratinocytes, isolated from neonatal foreskin, were grown on a feeder layer of mytomycin treated T3T mouse fibroblasts in Complete Media (DME+f-12, 1M Hepes, Adenine, Hydrocortisone, Cholera Toxin, Insulin, EGF, FBS, and Penn-Strep) and in the presence of 0.09 mM calcium. Following treatment with trypsin, keratinocytes were seeded at $15 \times 10^3$ cells/well in 12 well tissue culture plates (Costar) in 1000 µL of complete KSFM (keratinocyte serum-free medium from Life Technologies) containing 0.09 mM calcium.

After 96 hours of incubation, the medium was removed, and fresh medium was added along with 0.01% of a test agent, as indicated in Table 4, within KSFM. 48 hours after incubation with the test agent the medium was again removed and 1 ml of phosphate buffered saline containing 1 mM hydrogen peroxide was added to each well. 1 mM of ferrous sulfate was then added to begin the oxidation. After 90 minutes of incubation with this oxidant mixture, oxidation was quenched by the addition of BHT. Plates were then stored at −70° C. awaiting further analysis.

Lipid peroxidation products were measured as a marker of oxidative stress and normalized to the amount of cell DNA to account for proliferation.

DNA Assay:

Plates were removed from the freezer, media was aspirated. Plates were freeze fractured three times. Hoechst dye (10 µg/mL final concentration)was added to each well and plated were incubated in the dark. After 15 minutes of incubation, plates were read in a fluorimeter (excitation 360 nm and emission 460 nm).

Lipid Peroxidation:

Culture wells containing the cells oxidized in PBS were scraped and 2001 µL of sample was taken. The chromagen N-methyl-2-phenylindole reacts with the test sample in acid at 45 degrees C. Under the given conditions, one molecule of either MDA or 4-hydroxyalkenal will react with 2 molecules of the reagent to produce a stable chromophore with maximal absorbance at 586 nm. Results were expressed as (absorbance of untreated cells=100% lipid oxidation)/DNA absorbance, Untreated cells (no antioxidant) had peroxidation of 100% ±10.1. Alpha-tocopherol was used as a positive control.

The results that were obtained are summarized in Table 4.

TABLE 4

| TEST MATERIAL (0.01%) | % lipid oxidation/DNA (±STD) relative to water control [100%(±10.1)] |
|---|---|
| alpha-tocopherol | 61.4 (±8.9) |
| Total Guggulipid | 85.7 (±15.8) |
| Fraction #0 | 85.2 (±3.7) |
| Fraction #10 | 155.4 (±19.9) |
| Fraction #14 | 205.9 (±13.9) |
| Fraction #15 | 118.7 (±19.8) |
| Fraction #21 | 159.8 (±22.7) |
| Fraction #24 | 82.4 (±5.7) |
| Fraction #42 | 53.2 (±21.3) |
| Fraction #43 | 74.1 (±2.7)* |

TABLE 4-continued

| TEST MATERIAL (0.01%) | % lipid oxidation/DNA (±STD) relative to water control [100%(±10.1)] |
|---|---|
| Fraction #44 | 84.2 (±3.8) |
| C. Wightii | 167.2 (±46.0) | p-value was determined using Lotus 1-2-3 students t-test.
*p-value < 0.05 (statistically significant compared to untreated cells)

The results in Table 4 indicate that gugulipid and fractions 42–44 (alcoholic fractions) had an antioxidant activity as predicted by the chemical assay. Alcoholic fractions 42–44 had the highest antioxidant activity, approaching the antioxidant activity of alpha-tocopherol. C. wightii still did not have antioxidant activity. Some of the other fractions had good antioxidant activity, even though they had only marginal activity in the chemical assay. It should be noted the concentration tested in the in-vitro peroxidation assay was relatively high, i.e. twice as high as the lowest concentration tested in a sebocyte assay. It is believed that at the lower concentration, more differences in the activities of various fractions would have been observed. The reduced activity of fraction 44 compared to fractions 42 and 43 is probably due to the reduced concentration of any active material, because fraction 44 was the end portion of the alcoholic fraction. In any event, as noted above, gugulipid and the alcoholic fractions thereof did exhibit antioxidant activity.

The results in Example 4 demonstrate the criticality of using gugulipid from C. mukul, rather than guggal from C. wightii, in order to deliver antioxidant activity.

In Examples 1–4, when fractions of gugulipid were tested, alcoholic fractions had the highest antisebum and antioxidant activity. Gugulipid from C. mukul and alcoholic fractions of gugulipid from C. mukul had optimum dual antisebum and antioxidant activity.

EXAMPLE 5

TEST PRODUCT:

A toner containing gugulipid was formulated as follows:

| INGREDIENT | % w/w |
|---|---|
| Water | to 100% |
| Alcohol (SDA 40-B) | 35.00 |
| Green Tea | 1.00 |
| PEG-40 Hydrogenated Castor Oil | 1.00 |
| PPG-5-ceteth 20 (ethoxylated cetyl alcohol) | 1.00 |
| Gugulipid | 0.20 |

SUBJECTS: Panelists who were self-proclaimed to have oily skin were screened for participation using the Sebumeter. The women ranged between the ages of 18 and 55. From this group, 11 women who met requirements of having oily skin as defined by a site score average (3 Sebumeter readings) >150, were chosen to participate in the five week product evaluation.

Use of the topical acne medications (e.g., Retin A, Alpha Hydroxy/Fruit Acids products, alcoholic toners, and masks/ exfoliators) were suspended beginning one week prior to the study and continuing throughout the duration of the study.

TEST CONDITIONS: The test environment was set to maintain a room temperature of 73±1° F., and relative humidity of 45±10%.

PROCEDURE: Panelists were evaluated, once weekly, twice (except week one) each day over the five week period. After the initial evaluation which was used for baseline results, panelists were instructed to use a test product on half of their face for a total of three (3) weeks, followed by one (1) week of regression (no treatment). During the evaluation days, panelists were required to cleanse and NOT use test toner at least three (3) hours prior to AM evaluation periods. Panelists were also required NOT to wear make-up on foreheads throughout the day during evaluation periods. Panelists were required to be available for all evaluation times and agree not to touch, rub, or disturb the test site in anyway throughout the duration of the test day.

At the beginning of each evaluation period (8:30–11:30), panelists came having washed their foreheads, at least three (3) hours prior, with their regular facial cleanser/soap. Test site areas measuring approximately 18 $cm^2$ were located on the panelist's forehead immediately above each eyebrow line. Utilizing the split forehead design, morning values for each panelist were established through three Sebumeter (manufactured by Courage and Kahazaka, Koln, Germany, model #SM810) readings done within each test site area. The Sebumeter cassette was held in contact with the skin for 30 seconds while a constant pressure of 10N was applied. After the 30 seconds have counted down, the device beeps for the cassette to be placed back into it for a reading. In 1 second, the measured value flashes on the instrument. Two additional readings per site were acquired, with the average used as the panelist's AM score. Panelists were then allowed to apply a product, with the left/right site application balanced based on degree of oiliness across panelists. Test site areas were treated with Code 426, 881 or 502 as per the usage instructions. Additional Sebumeter readings were obtained at five (5) hours after treatment.

TREATMENT: Applications of test product occurred one to two times daily. They involved dispensing an ad lib amount of product using a cotton ball in a randomized half-face design.

ANALYSIS: The decoded and sorted data was analyzed using Lotus 123 and SAS software. Paired t-Tests (Treated–Untreated) were run on the data sets from each treatment group, at each evaluation time.

The results that were obtained are summarized in Table 5 below.

TABLE 5

DIFFERENCE VALUES

| PANELIST # | BASE AM TR-UNT | WEEK ONE AM TR-UNT | WEEK ONE PM TR-UNT | WEEK TWO AM TR-UNT | WEEK TWO PM TR-UNT | WEEK THREE AM TR-UNT | WEEK THREE PM TR-UNT | REGRESSION AM TR-UNT | REGRESSION PM TR-UNT |
|---|---|---|---|---|---|---|---|---|---|
| 1 | 23.7 | 46.0 | −25.7 | −6.3 | 3.7 | −8.0 | −121.0 | 6.0 | −51.0 |
| 2 | −6.7 | −61.7 | −23.7 | 074.0 | −11.3 | −25.0 | −20.0 | −25.3 | −56.0 |
| 3 | −39.0 | 33.7 | −4.7 | 33.0 | 8.0 | 0.3 | 10.0 | −30.7 | −11.0 |
| 4 | 27.7 | 17.3 | 11.7 | −68.3 | −29.0 | −79.0 | 1.3 | −24.0 | 3.7 |
| 5 | 22.3 | | | −28.7 | −63.7 | −45.0 | 19.0 | 30.0 | 0.0 |
| 6 | 23.3 | −39.0 | −84.7 | −26.7 | −24.3 | −7.0 | −4.3 | −26.3 | 3.0 |
| 7 | 52.0 | −79.3 | −65.0 | −70.0 | −52.3 | 31.0 | 39.0 | 24.3 | −29.7 |
| 8 | −19.7 | −19.3 | 6.0 | −30.3 | −39.3 | −15.0 | −89.0 | −19.0 | 63.0 |
| 9 | −12.3 | 4.7 | −18.0 | 4.7 | 13.7 | 54.7 | 33.3 | −2.0 | 0.0 |
| 10 | −37.3 | −29.3 | −10.7 | 30.7 | 10.0 | 44.3 | 44.7 | −17.0 | −44.0 |
| 11 | −17.0 | −18.3 | 8.7 | −37.0 | −64.0 | −96.0 | −9.7 | 15.0 | −12.0 |
| AVG | 1.5 | −14.5 | −20.6 | −24.8 | −22.6 | −13.2 | −8.8 | −6.3 | −12.2 |

RESULTS: The sites treated with Gugulipid scored lower than the untreated sites at all time periods. Average scores for the sites treated with Gugulipid ranged between 183 and 242 (baseline=227), while the average scores for the untreated sites ranged between 197 to 263 (baseline=225). According to a paired comparison of the treated minus untreated readings each evaluation time, only the Week 2 PM value for the group using toner with gugulipid was statistically ($p<0.05$) significantly different from zero, while the Week 1 PM value exhibited marginal ($p<0.10$) significance. The lack of statistical significance may be attributed to the high degree of variability in the data and the small sample size.

CONCLUSION: The application to the skin of women with increased sebum production of a toner with gugulipid led to consistently lower oil levels for treated sites compared to the untreated control sites.

Examples 6–9 illustrate topical compositions according to the present invention. The compositions can be processed in conventional manner. They are suitable for cosmetic use. In particular the compositions are suitable for application to oily, wrinkled, aged and/or photodamaged skin, to improve the appearance (radiance, clarity, finish) and feel thereof as well as for application to healthy skin to prevent or retard oiliness or deterioration thereof.

EXAMPLE 6

The following is a typical antisebum and anti-oxidant composition within the scope of the present invention:

Oil Controlling Lotion

| INGREDIENT | % W/W |
|---|---|
| DI Water | QS |
| Propylene Glycol | 1.000 |
| Xanthan Gum | 0.200 |
| Disodium EDTA | 0.100 |
| Methylparaben | 0.300 |
| Polysorbate 20 | 1.500 |
| Octyl Methoxycinnamate | 2.000 |
| Retinyl Linoleate | 0.100 |
| Tridecyl Salicylate | 2.000 |
| Gugulipid | 0.001 |
| Cetyl Alcohol | 1.500 |
| PEG-165 Glycerol Stearate | 3.000 |
| Propylparaben | 0.100 |

Oil Controlling Lotion -continued

| INGREDIENT | % W/W |
|---|---|
| Cyclomethicone | 15.000 |
| Dimethicone | 2.000 |
| Dimethiconol | 0.500 |
| Micronized Titanium Dioxide | 0.500 |
| Sodium Hyaluaronate 1% sln | 3.000 |
| Triethanolamine 99% | 0.200 |
| Salicyclic Acid | 0.200 |
| Phenoxyethanol | 0.350 |

EXAMPLE 7

A leave-on facial emulsion composition is prepared by combining the following components utilizing conventional mixing techniques.

| INGREDIENT | % WEIGHT |
|---|---|
| Water | qs |
| Glycerin | 3.00 |
| Cetyl Palmitate | 3.00 |
| Cetyi Alcohol | 1.26 |
| Glyceryl Monohydroxy Stearate | 0.74 |
| Dimethicone | 0.60 |
| Stearic Acid | 0.55 |
| Octyldodecyl Myristate | 0.30 |
| Potassium Hydroxide | 0.20 |
| Carbomer 1342 | 0.125 |
| Tetrasodium EDTA | 0.125 |
| DMDM Hydantoin and Iodopropynyl | 0.10 |
| Gugulipid | 0.10 |
| Carbomer 951 | 0.075 |

This emulsion is useful for providing control of sebum secretion and protecting the skin from free radical damage.

EXAMPLE 8

A leave-on facial emulsion composition is prepared by combining the following components utilizing conventional mixing techniques.

| INGREDIENT | % WEIGHT |
|---|---|
| Water | qs |
| Glycerin | 3.00 |
| Cetyl Palmitate | 3.00 |
| Cetyl Alcohol | 1.26 |
| Quaternium-22 | 1.00 |
| Glyceryl Monohydroxy Stearate | 0.74 |
| Dimethicone | 0.60 |
| Stearic Acid | 0.55 |
| Cyclomethicone and Dimethiconol | 0.50 |
| Octyldodecyl Myristate | 0.30 |
| Potassium Hydroxide | 0.20 |
| Carbomer 1342 | 0.125 |
| Tetrasodium EDTA | 0.10 |
| DMDM Hydantoin and Iodopropynyl | 0.10 |
| Alcoholic fraction of gugulipid | 0.05 |
| Carbomer 951 | 0.075 |

EXAMPLE 9

The following are additional examples of typical antisebum and anti-oxidant composition within the scope of the present invention:

| Chemical | % w/w |
|---|---|
| EXAMPLE 9A: Skin Cream (Oil in Water type) | |
| Water | qs |
| Disodium EDTA | 0.100 |
| Polysorbate 40 | 2.000 |
| Butylene Glycol | 3.000 |
| Glycerin | 5.000 |
| Methylparaben | 0.300 |
| Retinyl Palmitate | 0.300 |
| Gugulipid | 0.100 |
| Isopropyl Palmitate | 2.000 |
| Isostearyl Isostearate | 3.000 |
| Dimethicone, 200 cst | 2.000 |
| Cyclomethicone | 10.00 |
| Imidazolidinyl Urea | 0.200 |
| Polyacrylamide | 3.000 |
| EXAMPLE 9B: Skin Cream (Oil in Water type) | |
| Water | qs |
| Carbopol 1382 | 0.300 |
| Disodium EDTA | 0.100 |
| Tween 40 | 5.000 |
| Propylene Glycol | 1.000 |
| Glycerin | 3.000 |
| Methylparaben | 0.300 |
| Triethanolamine 99% | 0.300 |
| Tridecyl Salicylate | 1.200 |
| Retinol | 0.100 |
| Squalane | 1.000 |
| Alcoholic fraction of Gugulipid | 0.500 |
| Shea Butter | 0.500 |
| Cetyl Alcohol | 1.500 |
| Octyl Palmitate | 2.000 |
| C12-15 Alkyl Benzoate | 5.000 |
| Octyl Stearate | 2.000 |
| Silicone 344 Fluid (Cyclomethicone) | 2.000 |
| Imidazolidinyl Urea | 0.200 |
| EXAMPLE 9C: Skin Cream (Oil in Water type) | |
| Water | qs |
| Carbopol 1382 | 0.250 |
| Disodium EDTA | 0.100 |
| Butylene Glycol | 2.000 |
| Glycerin | 3.000 |
| Methylparaben | 0.250 |
| Triethanolamine 99% | 0.250 |
| Capric/Caprylic Triglyceride | 5.000 |
| Shea Butter | 0.500 |
| Cetyl Alcohol | 1.000 |

| Chemical | % w/w |
|---|---|
| PEG-100 Glycerol Monostearate | 4.000 |
| C12-15 Alkyl Benzoate | 6.000 |
| Tocopheryl Linoleate | 0.500 |
| Gugulipid | 0.250 |
| Silicone 200 Fluid (Dimethicone) | 2.000 |
| Imidazolidinyl Urea | 0.200 |
| EXAMPLE 9D: Micro Emulsion | |
| PPG-5-Ceteth-20 | 4.000 |
| PEG-40 Hydrogenated Castor Oil | 1.750 |
| Polyglyceryl-10 Decaoleate | 10.00 |
| PEG-8 Caprylic/Capric Glycerides | 10.00 |
| SDA Alcohol 40B | 12.00 |
| Isodecyl Neopentanoate | 16.00 |
| Glyceryl Trioctanoate | 8.000 |
| Cyclomethicone (DC 344 Fluid) | 8.000 |
| Propylparaben | 0.100 |
| Isostearic Acid | 2.500 |
| Tridecyl Salicylate | 2.500 |
| Alcoholic fraction of gugulipid | 0.300 |
| Phenoxyethanol | 0.300 |
| Deionized Water | QS |
| EXAMPLE 9E: Skin Cream (Water in Oil type) | |
| Cyclomethicone (DC 344 Fluid) | 12.000 |
| Dimethicone (DC 200/10 fluid) | 2.000 |
| Dimethicone Copolyol | 2.500 |
| Cetyl Dimethicone | 0.500 |
| C12-15 Alkyl Benzoate | 3.000 |
| Tridecyl Salicylate | 5.000 |
| Gugulipid | 0.500 |
| Glycerin | 3.000 |
| Propylene Glycol | 2.000 |
| Disodium EDTA | 0.100 |
| Methylparaben | 0.250 |
| Sodium Chloride | 1.200 |
| Phenoxyethanol | 0.200 |
| Deionized Water | QS |
| EXAMPLE 9F: Anhydrous Serum | |
| SD Alcohol 40 B (200 proof) | 20.00 |
| Cyclomethicone (DC 344 Fluid) | 2.500 |
| Squalene | 1.000 |
| Octyl Isononanoate | 2.500 |
| Dimethicone (DC 200 Fluid) | 5.200 |
| Isononyl Isononanoate | 30.00 |
| PEG-7 Glyceryl Cocoate | 1.000 |
| Polyglycerol Ricinoleate | 3.000 |
| Gugulipid | 1.000 |
| Butylene Glycol | 1.000 |
| Propylparaben | 0.100 |
| Dimethiconol | 2.750 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A method of obtaining an alcoholic fraction of gugulipid, comprising
   (a) mixing said gugulipid with petroleum ether,
   (b) separating the petroleum ether soluble components of gug ulipid from the non soluble components,
   (c) mixing the non soluble components from step (b) with alcohol, and (d) recovering the alcohol soluble components.

2. A method of reducing or preventing oily skin conditions, the method comprising applying to the skin a composition comprising (a) from about 0.0001 wt. % to about 10 wt. % of an antisebum agent of the alcohol soluble components of gugulipid obtainable by the method of claim 1, or a mixture of gugulipid and the alcohol soluble components of gugulipid; and (b) a cosmetically acceptable vehicle.

3. A method of reducing or preventing sebum secretions from sebocytes, the method comprising applying to the skin a composition comprising (a) from about 0.0001 wt. % to about 10 wt. % of an antisebum agent of the alcohol soluble components of gugulipid obtainable by the method of claim 1, or a mixture of gugulipid and the alcohol soluble components of gugulipid; and (b) a cosmetically acceptable vehicle.

4. A method of protecting skin from free radical activity, the method comprising applying to the skin a composition comprising (a) from about 0.0001 wt. % to about 10 wt. % of an anti-oxidant agent of the alcohol soluble components of gugulipid obtainable by the method of claim 1, or a mixture of gugulipid and the alcohol soluble components of gugulipid; and (b) a cosmetically acceptable vehicle.

5. The method of claim 4 wherein gugulipid is obtained from C. mukul.

6. A cosmetic composition comprising (a) from about 0.0001 wt. % to about 5 wt. % of the alcohol soluble components of gugulipid obtainable by the method of claim 1; and (b) a cosmetically acceptable vehicle.

7. A method of obtaining a dual benefit of (i) reducing or preventing oily skin conditions and (ii) protecting skin from free radical activity, the method comprising applying to the skin a composition comprising (a) from about 0.0001 wt. % to about 10 wt. % of gugulipid obtained from C. mukul; and (b) a cosmetically acceptable vehicle.

* * * * *